United States Patent [19]

Chan

[11] Patent Number: 4,757,005
[45] Date of Patent: Jul. 12, 1988

[54] METHOD AND CELL LINE FOR OBTAINING PLASMINOGEN ACTIVATORS

[75] Inventor: Sham Y. Chan, Osceola, Ind.

[73] Assignee: Miles Inc., Elkhart, Ind.

[21] Appl. No.: 704,593

[22] Filed: Feb. 22, 1985

Related U.S. Application Data

[63] Continuation-in-part of Ser. No. 601,868, Apr. 19, 1984, abandoned.

[51] Int. Cl.$^4$ .......................... C12P 21/00; C12N 5/00
[52] U.S. Cl. ....................................... 435/68; 435/70; 435/240.2; 435/240.31
[58] Field of Search .................... 435/68, 70, 212–219, 435/226, 240, 241; 424/94; 530/350, 380, 381

[56] References Cited

U.S. PATENT DOCUMENTS

| | | | |
|---|---|---|---|
| 3,904,480 | 9/1975 | Hull | 435/217 |
| 4,232,124 | 11/1980 | Mann | 435/212 |
| 4,335,215 | 6/1982 | Tolbert | 435/241 |
| 4,505,893 | 3/1985 | Mori | 424/94 |
| 4,537,860 | 8/1985 | Tolbert | 435/240 |
| 4,550,080 | 10/1985 | Hasegawa | 435/212 |
| 4,552,760 | 11/1985 | Murakami | 424/94 |
| 4,582,826 | 4/1986 | Inada | 514/182 |

OTHER PUBLICATIONS

Matsuo, O. et al., Acta Haematol, Japan, 47:1049–1053 (1984).
Kaign, M. E. et al., Proc. Natl. Acad. Sci., U.S.A., 78(9):5673–5676 (9–1981).
Rijken, D. et al., Journal of Biological Chemistry, 256(13):7035–7041 (7–1981).
Ossowski, L. et al., Cancer Research, 40:2310–2315 (7–1980).
Barnes, D. et al., Nature (10–1979).
Rosenthal, K. L. et al., Molecular & Cellular Biochemistry, 15(2): 149–153 (4–1977).
Collen, D. et al., Thromb. Haemostasis, 48(3):294–296 (1982).
Levin, E. G. et al., Cell, 22(3):701–708 (1980).
Lewis, L. J. Thrombosis Haemostasis, 42:895–900 (1979).
Davis, B. et al., *Microbiology*, Third Edition, Harper & Row, Inc., Philadelphia (1980), pp. 942–953.
Ham, R. G., *Cold Spring Harbor Conferences on Cell Proliferation*, vol. 9, pp. 39–60 (1982).

*Primary Examiner*—Margaret Moskowitz
*Attorney, Agent, or Firm*—Mary G. Boguslaski; Edward P. Gray

[57] ABSTRACT

A method of increasing the yield of plasminogen activator from a plasminogen activator-producing cell line by adapting said cell line to grow in a suitable growth medium essentially free of fetal calf serum is disclosed. Also disclosed are cell lines capable of producing relatively large quantities of plasminogen activator, and a chemically defined growth medium suitable for adapting a plasminogen activator-secreting cell line to growth in the absence of fetal calf serum.

17 Claims, No Drawings

METHOD AND CELL LINE FOR OBTAINING PLASMINOGEN ACTIVATORS

This application is a continuation-in-part of application Ser. No. 601,868, filed Apr. 19, 1984 now abandoned.

BACKGROUND OF THE INVENTION

Plasminogen activator (PA) is a serine protease which exerts its action through hydrolysis of the $Arg_{560}$–$Val_{561}$ peptide bond in plasminogen, yielding the 2-chain plasmin molecule. Plasmin has a general proteolytic activity and in the physiological environment of circulating blood it attacks mainly fibrin. Plasminogen activator plays a key role in the fibrinolytic system, which by lysing intra- or extra-vascular thrombi, clots, or fibrinous deposits, profoundly influences the incidence of thromboembolic vascular disease and its outcome.

Plasminogen activators have been isolated from body fluids such as blood and urine, and solid tissues of various histologic origin. Mammalian cell cultures are also known to produce plasminogen activators. There may be large differences in the amounts of plasminogen activator produced by cell lines derived from different tissues of the same animal, by cells of the same histologic type derived from cells of a single type independently transformed with the same oncogenic agent.

There is an urgent need for obtaining cells which are capable of producing increased amounts of PA and establishing techniques which would improve the process of using animal cell culture to produce PA on an industrial scale.

DESCRIPTION OF PERTINENT ART

European patent application No. 113,319 A2 discloses human cell lines capable of proliferating in the absence of serum and other macromolecular growth factors as well as the method utilized for producing such cell lines. European patent application No. 112,174 A2 describes a serum-free medium capable of growing a wide range of suspension and monolayer cells, said medium containing fetuin, transferrin and a substituted phosphatidyl-choline.

As taught in *J. Biol. Chem.*, 256, 7035–7041 (1981), it is well-known that human cell lines of neoplastic origins, e.g. melanoma cells, can produce substantial amounts of PA.

Malignant cell lines such as cervix carcinoma, larnyx carcinoma, epidermoid carcinoma of the oral cavity, colon and rectum carcinoma cells have been shown to produce PA (see *Molecular Cellular Biochemistry*, Vol. 15, No. 2, pages 149–153 (1977).

In *Proc. Natl. Acad. Sci.*, Vol. 78, No. 9, pages 5673–5676 (1981), it is reported that two metastatic prostatic carcinoma cell lines, PC-3 and DU-145, have been grown in long-term culture in a defined medium free of serum, hormones or growth factors.

A progressive loss of metastatic potential and tumorigenicity was noted following serial passage in vitro of human epidermoid carcinoma. However, with regard to PA, high levels of production were well-correlated with retention of tumorigenicity and metastasis, *Cancer Research*, 40, 2310–2315 (1980).

Barnes and Sato in "Growth of a Human Mammary Tumour Cell Line in a Serum-Free Medium" (*Nature*, October 1979) report the growth of the MCF-7 cell line in a serum-free medium supplemented with insulin, transferrin, epidermal growth factor, prostagladin $F_{2\alpha}$ and cold-insoluble globulin. The synthetic nutrient medium used in this study was 1:1 mixture of Ham's F-12 and Dulbecco-modified Eagle's medium supplemented with antibiotics, sodium bicarbonate, HEPES and sodium selenite.

None of these references suggest or teach that the yield of PA from PA-secreting cells can be increased by adapting such cells to grow in a medium which is essentially free of fetal calf serum.

SUMMARY OF THE INVENTION

The present invention is directed to a method of increasing the yield of plasminogen activator (PA) obtained from a PA-producing cell line, and a cell line capable of producing relatively large amounts of PA. The method involves growing PA-producing cells in a suitable growth medium containing fetal calf serum (bovine serum) and adapting the cells to grow in said suitable growth medium essentially free of fetal calf serum by passing the cells through a series of said growth media containing decreasing amounts of fetal calf serum.

A biologically pure tissue culture, capable of producing relatively large quantities of plasminogen activator is a human prostate adenocarcinoma, available from the American Type Culture Collection (ATCC) designated as Cell Repository Line (CRL)-1435. Other biologically pure tissue cultures capable of producing relatively large quantities of plasminogen activator when adapted according to the method of the present invention are ATCC CRL-1622 and ATCC CRL-1579.

DETAILED DESCRIPTION OF THE INVENTION

It is well-known that plasminogen activators can be produced by tumor cells in culture. Examples of tumor cells from mammals which can be used in the present invention include melanoma, prostate, breast, colon, ovarian, pancreatic, cervical, rectal, endometrial and fibroblastic tumor cell lines. Preferred cell lines are human carcinoma cell lines such as melanoma, prostate, breast, colon, ovarian, pancreatic and endometrial. Suitable carcinoma cell lines are available from depositories such as American Type Culture Collection, 1201 Parklawn Drive, Rockville, MD 20852 or can be obtained from numerous researchers at universities, hospitals or research institutes. The identity of the carcinoma cell line is not of critical importance; the present method allows the amount of PA obtained from a PA producing cell line to be increased by as much as from about 5 to about 60 fold. As indicated herein, a preferred high-yield producer of PA is a human prostate adenocarcinoma, ATCC CRL-1435. Other preferred biologically pure tissue cultures capable of producing relatively large quantities of plasminogen activator when adapted according to the method of the present invention are ATCC CRL-1622 and ATCC CRL-1579.

As used herein, the phrase "suitable growth medium" refers to a medium such as described in detail hereinafter containing a mixture of Waymouth's MB752/1, Dulbecco Minimal Essential Medium (MEM) and Ham's F-12 medium in a ratio (by weight) of from about 1:1:1 to about 3:1:2, respectively.

The method involves selecting a parent carcinoma cell line which produces PA, and growing the cell line to confluency in a suitable growth medium which contains at the outset from about 5 to about 20 percent fetal calf serum. After the cell line reaches confluency, the cells are removed, usually by trypsinization and subjected to subculturing in a series of suitable growth media which contain decreasing amounts of fetal calf serum. The rate of removal of the fetal calf serum can be easily determined by sequentially reducing the calf serum and examining the viability of the cell growth. For example, the parent cells can be grown in a suitable growth medium containing approximately 10 percent fetal calf serum to confluency. The cells are then removed and subcultured through at least one passage in a suitable growth medium containing approximately 5 percent fetal calf serum. After the cells reach confluency, the cells can be removed again and subcultured through at least one passage in a suitable growth medium containing approximately 2.5 percent fetal calf serum. This procedure can be repeated until the suitable growth medium used is essentially free of fetal calf serum. In the present invention, sequential reduction by a 2-fold factor has been found to be a preferred method.

It has been found that various combinations of commercially available growth media are suitable for use in the present invention. However, as the concentration of fetal calf serum is decreased, the suitable growth medium used in the method of the present invention must be correspondingly supplemented with the following growth factors: fetuin, bovine serum albumin, insulin, transferrin, 5α-dihydrotestosterone and dexamethasone. The point during the sequential reduction of fetal calf serum at which these growth factors must be added may be readily determined by one skilled in the art and will vary depending on factors such as the type of cell lines being cultured and the specific conditions under which the culturing is being carried out. Suffice it to say that the growth factors must be added at a point when cell viability might otherwise be threatened due to the decreased concentration of fetal calf serum; however, when the suitable culture medium contains a sufficient concentration of fetal calf serum to sustain the growth of the cell line, addition of the growth factors noted above is unnecessary and may lead to subsequent difficulty in adapting the cell line to grow in the suitable serum-free growth medium.

A suitable growth medium for use as described herein can be obtained by mixing together Waymouth's MB752/1 medium, Dulbecco MEM and Ham's F-12 medium, commercially available from GIBCO Laboratories, Grand Island, New York. The ratio (by weight) can range from 1:1:1 to 3:1:2, respectively.

A preferred medium, hereinafter referred to as "SYC" medium, is composed of a 1:1:1 (by weight) mixture of Waymouth's MB752/1, Dulbecco MEM, and Ham's F-12, respectively. It has been observed that cell growth is optimized when the suitable growth medium used is SYC medium.

In the total absence of Waymouth's MB752/1, cell growth is greatly retarded. These media have the compositions as set forth in Table I.

TABLE I

| | (Concentration of each component in mg/l) | | | |
|---|---|---|---|---|
| | Waymouth MB752/1 | Ham's F-12 | Dulbecco MEM | SYC Medium |
| $CaCl_2$ (anhydrous) | 90.61 | 33.22 | 200 | 107.94 |
| $CuSO_4.5H_2O$ | — | 0.00249 | — | 0.00083 |
| $Fe(NO_3)_3.9H_2O$ | — | — | 0.1 | 0.033 |
| $FeSO_4.7H_2O$ | — | 0.834 | — | 0.278 |
| KCl | 150 | 223.6 | 400 | 257.87 |
| $KH_2PO_4$ | 80 | — | — | 26.67 |
| $MgCl_2$ | 112.56 | 57.22 | — | 56.59 |
| $MgSO_4$ | 97.67 | — | 97.67 | 65.11 |
| NaCl | 6000 | 7599 | 6400 | 6666.33 |
| $Na_2HPO_4$ | 300 | 142.04 | — | 147.35 |
| $NaH_2PO_4.H_2O$ | — | — | 125 | 41.67 |
| $ZnSO_4.7H_2O$ | — | 0.863 | — | 0.288 |
| L-Alanine | — | 8.9 | — | 2.97 |
| L-Arginine HCl | 75 | 211 | 84 | 123.33 |
| L-Asparagine.$H_2O$ | — | 15.01 | — | 5.0 |
| L-Aspartic acid | 60 | 13.30 | — | 24.43 |
| L-Cystine.2HCl | 19.55 | — | 62.57 | 27.37 |
| L-Cysteine HCl.$H_2O$ | 100.26 | 35.12 | — | 45.13 |
| L-Glutamic acid | 150 | 14.7 | — | 54.9 |
| L-Glutamine | 350 | 146 | 584 | 360 |
| L-Glycine | 50 | 7.5 | 30 | 29.17 |
| L-Histidine HCl.$H_2O$ | 164.1 | 20.96 | 42 | 75.69 |
| L-Isoleucine | 25 | 3.94 | 105 | 44.65 |
| L-Leucine | 50 | 13.10 | 105 | 56.03 |
| L-Lysine HCl | 240 | 36.5 | 146 | 140.83 |
| L-Methionine | 50 | 4.48 | 30 | 28.16 |
| L-Phenylalanine | 50 | 4.96 | 66 | 40.32 |
| L-Proline | 50 | 34.5 | — | 28.17 |
| L-Serine | — | 10.5 | 42 | 17.50 |
| L-Threonine | 75 | 11.9 | 95 | 60.63 |
| L-Tryptophane | 40 | 2.04 | 16 | 19.35 |
| L-Tyrosine (Na salt) | 57.66 | 7.78 | 103.79 | 56.41 |
| L-Valine | 65 | 11.70 | 94 | 56.9 |
| Ascorbic acid | 17.5 | — | — | 5.83 |
| Biotin | 0.02 | 0.0073 | — | 0.0091 |
| Ca pantothenate | 1.0 | 0.48 | 4.0 | 1.83 |
| Choline Cl | 250 | 13.96 | 4.0 | 89.32 |
| Folic acid | 0.4 | 1.30 | 4.0 | 1.9 |
| i-Inositol | 1.0 | 18.0 | 7.2 | 8.73 |
| Nicotinamide | 1.0 | — | 4.0 | 1.67 |
| Niacinamide | — | 0.037 | — | 0.012 |
| Pyridoxine HCl | 1.0 | 0.062 | 4.0 | 1.69 |
| Riboflavin | 1.0 | 0.038 | 0.40 | 0.48 |

TABLE I-continued

| | (Concentration of each component in mg/l) | | | |
|---|---|---|---|---|
| | Waymouth MB752/1 | Ham's F-12 | Dulbecco MEM | SYC Medium |
| Thiamine HCl | 10.0 | 0.34 | 4.0 | 4.78 |
| Vit. $B_{12}$ | 0.2 | 1.36 | — | 0.52 |
| D-Glucose | 5000 | 1802 | 1000 | 2600 |
| Glutathione (reduced) | 15 | — | — | 5 |
| Hypoxanthine (Na salt) | 29 | 4.77 | — | 11.26 |
| Phenol red | 10 | 1.2 | 15 | 8.73 |
| Thymidine | — | 0.73 | — | 0.24 |
| Linoleic acid | — | 0.084 | — | 0.028 |
| Lipoic acid | — | 0.21 | — | 0.07 |
| Putrescine.2HCl | — | 0.161 | — | 0.054 |
| Na pyruvate | — | 110 | 110 | 73.33 |

As described herein, as the concentration of fetal calf serum is serially decreased in each passage, it becomes necessary to supplement the suitable growth medium with from about 50–150 mg/l fetuin; from about 50–150 mg/l bovine serum albumin; from about 5–10 mg/l insulin; from about 5–40 mg/l transferrin; from about 50–200 μg/l 5α-dihydrotestosterone; and from about 50–200 μg/l dexamethasone. It has been observed that insulin and transferrin are critical growth factors without which the cells will die after one passage where all growth factors would otherwise have been added to supplement the suitable growth medium.

The following examples are provided as a means of illustrating the present invention and should not be construed as a limitation thereon.

EXAMPLE I

Following receipt from the depository, a human prostate adenocarcinoma, ATCC CRL-1435, was stabilized by growing to confluency in Earle's Minimal Essential Medium (MEM) commercially available from GIBCO. This procedure was carried out by placing a 25 ml portion of MEM plus 10 percent fetal calf serum in a 175 ml culture flask, maintained at 37° C. in a 5 percent $CO_2$ atmosphere, and adding $5 \times 10^5$ of the above adenocarcinoma cells. The parent cells were removed from the flask by adding a 5 ml portion of 0.25 percent trypsin.

The parent cells from the above stabilization procedure were then added to a previously prepared quantity of SYC medium containing 10 percent fetal calf serum and were maintained at 37° C. The cells reached confluency in approximately one week after which they were removed by trypsinization as described above and were added to a quantity of SYC medium containing 5 percent fetal calf serum. The cells were again maintained at 37° C. until they reached confluency. This procedure was repeated twice using SYC medium containing 2.5 percent and 1.25 percent fetal calf serum, respectively. At the 1.25 percent fetal calf serum concentration, the SYC medium was supplemented with fetuin (75 mg/l), bovine serum albumin (75 mg/l), insulin (8 mg/l), transferrin (25 mg/l), 5α-dihydrotestosterone (100 μg/l) and dexamethasone (100 μg/l). The cells reached confluency in approximately ten days.

The cells were then passaged into SYC medium containing the same growth factors as in the 1.25 percent fetal calf serum passage, except that no fetal calf serum was present. The cells reached confluency in approximately one week.

The above cells were then passaged ten times through SYC medium (containing the same growth factors as above), free of fetal calf serum, until the cell line stabilized. Determination of stabilization was achieved by observing the same growth pattern during each passage and the amount of PA produced. After ten passages, the biologically pure altered confluent cells, designated PC-3f, and deposited with ATCC having accession number CRL-8539 were assayed for PA production by the following procedure (as described in *Progress in Chemical Fibrinolysis and Thrombolysis*, Vol. 3, pages 315–322; 1978).

A 100 μl portion of culture fluid (obtained after confluency) was incubated with 100 μl of human plasminogen (0.33 mg/ml) for 15 minutes at 37° C. after which 250 μl of Tris buffer (0.1 M Tris; 0.2 M NaCl; pH 7.4) and 250 μl of 1 mM tripeptide substrate (Valleu-lys-p-nitro-anilide; Kabi, Stockholm, Sweden) were added. This mixture was incubated for an additional 3 minutes after which the reaction was stopped by the addition of 100 μl of 50% acetic acid. The absorbance of the reaction mixture was read at 405 nm and was then compared to a urokinase standard curve generated with commercially available urokinase (Calbiochem., La Jolla, CA) using the same assay procedure. This assay technique allows quantitation of the PA produced by the cells by measuring the quantity of plasmin produced by activation of the plasminogen from the PA present in the culture fluid.

The test results are set forth in Table II. The amount of PA produced by the cells is expressed in CTA units per ml of culture fluid as stipulated by the Committee on Thrombolytic Agents of the National Heart Institute, as described in *Thromb. Diath. Haemor.*, 21, page 259 (1969). As a control, the PA activity of the parent cell line (ATCC-1435) was also determined.

TABLE II

| | (PA activity expressed in CTA Units/ml) | | |
|---|---|---|---|
| Cell Line | 48 Hours | 72 Hours | 96 Hours |
| ATCC CRL-1435 | 11.5 | 18.5 | Died |
| PC-3f (ATCC CRL-8539) | 28.5 | 45.0 | 70.4 |

As shown in the above test results, passage of the parent cell line through serum-free medium produced a cell line which yielded up to 70.4 CTA Units of PA, as compared to a maximum of 18.5 CTA Units of PA produced by the parent cell line, an increase of approximately 4-fold. Advantageously, the altered cell line was viable for an additional 24 hours.

EXAMPLE II

The procedure described in Example I was repeated using as a parent cell line a human pancreatic carcinoma cell line, ATCC-1420. The biologically pure altered cells obtained by the procedures described herein were designated as PaCa-2f and were deposited with ATCC having accession number ATCC CRL-8725. Test results obtained are summarized in Table III below:

TABLE III

| | (PA activity expressed in CTA Units/ml) | | |
|---|---|---|---|
| Cell Line | 48 Hours | 72 Hours | 96 Hours |
| ATCC-1420 | 2.5 | 7.5 | Died |
| PaCa-2f (ATCC CRL-8725) | 5.4 | 15.0 | 25.2 |

As shown in the test results, passage of the parent cell line through serum-free medium produced a cell line which yielded PA up to 25.2 CTA Units, an increase of approximately 3-fold, as well as a 24 hour increase in viability.

EXAMPLE III

The procedure described in Example I was repeated using as a parent cell line a mouse melanoma cell line, B-16, available from Jackson Lab., Bar Harbor, Maine. The biologically pure altered cells obtained by the procedure described herein were designated as B-16f. Test results obtained are summarized in Table IV below:

TABLE IV

| | (PA activity expressed in CTA Units/ml) | | | |
|---|---|---|---|---|
| Cell Line | 24 Hours | 48 Hours | 72 Hours | 96 Hours |
| B-16 | 0.70 | 1.20 | Died | — |
| B-16f | 2.30 | 2.80 | 3.0 | 3.2 |

The biologically pure altered cell line showed a 3-fold increase in PA production at 24 hours and a 2-fold increase in PA production at 48 hours. Further, the altered cell line was viable for up to 96 hours.

EXAMPLE IV

The procedure described in Example I was repeated using as a parent cell line ATCC CRL-1622, an endometrial adenocarcinoma cell line available from the ATCC. The biologically pure altered cells obtained by the method of the present invention were designated as KLEf and were deposited with ATCC having accession number ATCC CRL-8726. PA activity was measured at 48 hours after the cells reached confluency and the results obtained are shown in Table V.

TABLE V

| (PA activity expressed in CTA Units/ml) | |
|---|---|
| Cell Line | 48 Hours |
| ATCC CRL-1622 | 0.05 |
| KLEf (ATCC CRL-8726) | 3.03 |

As shown in Table V, the altered cell line, KLEf, showed over a 60-fold increase in PA production over the parent cell line at 48 hours.

EXAMPLE V The procedure described in Example I was repeated using as a parent cell line an amelanotic melanoma cell line available from ATCC under accession number ATCC CRL-1579. The biologically pure altered cells obtained by the method of the present invention were designated MLf and were deposited with ATCC having accession number ATCC CRL-8724. PA activity was measured at 48 hours after the cells reached confluency and the results obtained are shown in Table VI.

TABLE VI

| (PA activity expressed in CTA Units/ml) | |
|---|---|
| Cell Line | 48 Hours |
| ATCC CRL-1579 | 0[a] |
| MLf (ATCC CRL-8724) | 0.07 |

[a]Activity level was below detection limits of the assay.

What is claimed is:
1. A method for increasing the yield of plasminogen activator obtained from plasminogen activator-producing mammalian tumor cells which comprises the steps of:
(a) growing said cells in a suitable growth medium supplemented with fetal calf serum, said suitable growth medium composed of a mixture of Waymouth's MB752/1, Dulbecco Minimal Essential Medium and Ham's F-12 medium in a ratio (by weight) of from about 1:1:1 to about 3:1:2, respectively,;
(b) passing said cells through a series of said suitable growth media containing decreasing amounts of fetal calf serum, said media supplemented with the growth factors fetuin, bovine serum albumin, insulin, transferrin, 5α-dihydrotestosterone and dexamethasone;
(c) growing said cells to confluency in said suitable growth medium essentially free of fetal calf serum and supplemented with said growth factors, said cells producing plasminogen activator at levels greater than that of the initial plasminogen activator-producing cells; and
(d) recovering therefrom said plasminogen activator.
2. The method of claim 1 wherein the plasminogen activator-producing cells are mammalian tumor cells selected from the group consisting of melanoma, prostate, breast, colon, ovarian, pancreatic, cervical, rectal, endometrial and fibroblastic tumor cells.
3. The method of claim 2 wherein the mammalian tumor cells are human carcinoma cell lines selected from the group consisting of melanoma, prostate, breast, colon, ovarian, pancreatic and endometrial cell lines.
4. The method of claim 3 wherein the tumor cell line is a human prostate adenocarcinoma.
5. The method of claim 1 wherein the suitable growth medium is an SYC medium composed of a 1:1:1 by weight mixture of Waymouth's MB752/1, Dulbecco MEM and Ham's F-12, respectively.
6. The method of claim 5 wherein the fetuin is present in a concentration of from 50–150 milligrams per liter; the bovine serum albumin is present in a concentration of from 50–150 milligrams per liter; the insulin is present in a concentration of from 5–10 milligrams per liter; the transferrin is present in a concentration of from 5–40 milligrams per liter; the 5α-dihydrotestosterone is present in concentration of from 5–200 micrograms per liter;

and the dexamethasone is present in a concentration of from 50–200 micrograms per liter.

7. The method of claim 6 wherein the fetuin is present in a concentration of 75 milligrams per liter; the bovine serum albumin is present in a concentration of 75 milligrams per liter; the insulin is present in a concentration of 8 milligrams per liter; the transferrin is present in a concentration of 25 milligrams per liter; the 5α-dihydrotestosterone is present in a concentration of 100 micrograms per liter; and the dexamethasone is present in a concentration of 100 micrograms per liter.

8. The method of claim 1 wherein the concentration of fetal calf serum is serially decreased by a 2-fold factor through each of said passages.

9. A method for increasing the yield of plasminogen activator obtained from human prostate adenocarcinoma cell line ATCC CRL-1435 which comprises the steps of:
(a) growing said cell line in a suitable growth medium supplemented with fetal calf serum, said suitable growth media composed of a mixture of Waymouth's MB752/1, Dulbecco Minimal Essential Medium and Ham's F-12 Medium in a ratio (by weight) of from about 1:1:1 to about 3:1:2, respectively;
(b) passing said cell line through a series of said suitable growth media containing decreasing amounts of fetal calf serum, said media supplemented with the growth factors fetuin, bovine serum albumin, insulin, transferrin, 5α-dihydrotestosterone and dexamethasone;
(c) growing said cell line to confluency in said suitable growth medium essentially free of fetal calf serum and supplemented with said growth factors, said cell line producing plasminogen activator at levels greater than that of the initial plasminogen activator-producing cell line; and
(d) recovering therefrom said plasminogen activator.

10. The method of claim 9 wherein said suitable growth medium is an SYC medium composed of a 1:1:1 by weight mixture of Waymouth's MB752/1, Dulbecco MEM and Ham's F-12, respectively.

11. The method of claim 10 wherein the fetuin is present in a concentration of from 50–150 milligrams per liter; the bovine serum albumin is present in a concentration of from 50–150 milligrams per liter; the insulin is present in a concentration of from 5–10 milligrams per liter; the transferrin is present in a concentration of from 5–40 milligrams per liter; the 5α-dihydrotestosterone is present in a concentration of from 50–200 micrograms per liter; and the dexamethasone is present in a concentration of from 50–200 micrograms per liter.

12. The method of claim 11 wherein the fetuin is present in a concentration of 75 milligrams per liter; the bovine serum albumin is present in a concentration of 75 milligrams per liter; the insulin is present in a concentration of 8 milligrams per liter; the transferrin is present in a concentration of 25 milligrams per liter; the 5α-dihydrotestosterone is present in a concentration of 100 micrograms per liter; and the dexamethasone is present in a concentration of 100 micrograms per liter.

13. The method of claim 9 wherein the concentration of fetal calf serum is serially decreased by a 2-fold factor through each of said passages.

14. A biologically pure culture of a plasminogen activator-secreting cell line designated as PC-3f having ATCC accession number CRL-8539.

15. A biologically pure culture of a plasminogen activator-secreting cell line designated as PaCa-2f having ATCC accession number CRL-8725.

16. A biologically pure culture of a plasminogen activator-secreting cell line designated as KLE$_f$ having ATCC accession number CRL-8726.

17. A biologically pure culture of a plasminogen activator-secreting cell line designated as ML$_f$ having ATCC accession number CRL-8724.

* * * * *